United States Patent
Lochead et al.

(10) Patent No.: US 6,407,095 B1
(45) Date of Patent: Jun. 18, 2002

(54) 1,4-DIAZABICYLO[3,2,2]NONANE DERIVATIVES, THEIR PREPARATION AND THEIR THERAPEUTIC APPLICATION

(75) Inventors: Alistair Lochead, Charenton; Samir Jegham, Montferrier sur Lez; Alain Nedelec, Colombes; Frédéric Galli, Vaucresson; Jean Jeunesse; Luc Even, both of Paris, all of (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/856,945

(22) PCT Filed: Dec. 1, 1999

(86) PCT No.: PCT/FR99/02975

§ 371 (c)(1),
(2), (4) Date: Jul. 16, 2001

(87) PCT Pub. No.: WO00/34279

PCT Pub. Date: Jun. 15, 2000

(30) Foreign Application Priority Data

Dec. 4, 1998 (FR) .............................................. 98 15326

(51) Int. Cl.[7] .................... C07D 471/08; A61K 31/551; A61P 25/28

(52) U.S. Cl. ........................................ 514/221; 540/567
(58) Field of Search ........................... 540/567; 514/221

(56) References Cited

U.S. PATENT DOCUMENTS 5,478,939 A 12/1995 Tryulski et al. ............. 544/349

FOREIGN PATENT DOCUMENTS

EP 0400661 12/1990
WO WO 96/30372 10/1996

OTHER PUBLICATIONS

DeCosta et al., J. Med. Chem., 36(16), 1993, pp. 2311–2320

*Primary Examiner*—Richard L. Raymond
*Assistant Examiner*—Venkataraman Balasubramanian
(74) *Attorney, Agent, or Firm*—Michael D. Alexander; Paul E. Dupont

(57) ABSTRACT

The invention relates to 1,4-diazabicyclo[3.2.2]nonane derivatives, to pharmaceutical compositions containing them, and to methods for the treatment or prevention of disorders associated with a dysfunction of the nicotinic receptors utilizing them.

5 Claims, No Drawings

1,4-DIAZABICYLO[3,2,2]NONANE DERIVATIVES, THEIR PREPARATION AND THEIR THERAPEUTIC APPLICATION

The compounds of the present invention correspond to the general formula (I)

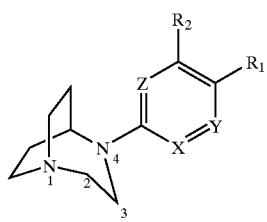

in which
one of the symbols X, Y and Z represents a nitrogen atom, another represents a group of formula C—$R_3$ and the third represents a nitrogen atom or a group of formula C—$R_4$, $R_3$ and $R_4$ represent, independently of each other, a hydrogen or halogen atom or a trifluoromethyl, cyano, hydroxyl, ($C_1$–$C_6$)alkyl or ($C_1$–$C_6$)alkoxy group.

$R_1$ and $R_2$ represent, independently of each other, a hydrogen or halogen atom or a trifluoromethyl, cyano, hydroxyl, ($C_1$–$C_6$)alkyl or ($C_1$–$C_6$)alkoxy group or a phenyl group optionally substituted with a halogen atom, with a trifluoromethyl group, with a cyano group, with a nitro group, with a hydroxyl group, with a ($C_1$–$C_6$)alkyl group, with a ($C_1$–$C_6$)alkoxy group, with an acetyl group, with a methylenedioxy group, with a trifluoromethoxy group, with a methylthio group or with a phenyl group.

The compounds of the invention can exist in the form of bases or of addition salts with acids.

The preferred compounds are those in the formula of which the heterocycle containing X, Y and Z is a 3-pyridyl or 3-pyridazinyl group.

In accordance with the invention, and according to the scheme which follows, the compounds of general formula (I) can be prepared by reacting 1,4-diazabicyclo[3.2.2] nonane, of formula (II), with a heterocyclic compound of general formula (III), in which X, Y, Z, $R_1$ and $R_2$ are as defined above and W represents a halogen atom.

A Buchwald coupling (J. Org. Chem. (1997) 62 6066–6068) can thus be carried out in the presence of a palladium catalyst such as palladium acetate, tris (dibenzylideneacetone)dipalladium(0), etc., a complexation ligand such as triphenylphosphine, tributylphosphine or 2,2'-bis(diphenylphosphino)-1,1'-binaphthyl, and a base, for example an organic base such as sodium t-butoxide, or an inorganic base such as caesium carbonate.

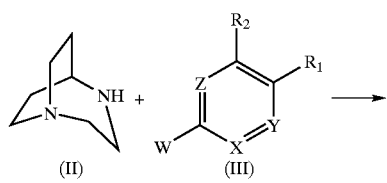

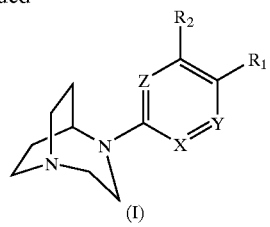

When X or Z represents a nitrogen atom, a nucleophilic substitution reaction can also be carried out in the presence of a strong base such as caesium carbonate or triethylamine.

1,4-Diazabicyclo[3.2.2]nonane is described in J. Med. Chem. (1993) 36 2311–2320.

For certain compounds, the substituents $R_1$ and/or $R_2$ are not present in the starting compound of general formula (III); depending on their nature, these substituents can be introduced onto the final compound of general formula (I). Thus, for example, compounds of general formula (I) in which $R_1$ and/or $R_2$ represent aryl groups, can be prepared from the corresponding compounds, in the formula of which $R_1$ and/or $R_2$ represent bromine or iodine atoms, according to any known method, such as a Suzuki coupling in the presence of a boronic acid and a palladium catalyst, for example tetrakis(triphenylphosphine)palladium.

The compounds of general formula (III) are commercially available or are accessible by methods described in the literature.

The examples which follow illustrate the preparation of a number of compounds of the invention. The elemental microanalyses and the IR and NMR spectra confirm the structures of the compounds obtained.

The numbers given in parentheses in the example titles correspond to those in the first column of Table 1 given later.

In the compound names, the hyphen "—" forms part of the name, and the underscore mark "_" serves merely to indicate the line break; it should be removed if a line break does not occur at that point, and should not be replaced either by a normal hyphen or by a space.

EXAMPLE 1

Compound 1

4-Pyrid-3-yl-1,4-diazabicyclo[3.2.2]nonane Hydrobromide (2:1)

1.0 g (7.92 mmol) of 1,4-diazabicyclo_[3.2.2]nonane, 5.0 g (31.7 mmol) of 3-bromopyridine, 88.9 mg (0.396 mmol) of palladium(II) acetate, 247 mg (0.396 mmol) of 2,2'-bis(diphenylphosphino)-1,1'-binaphthyl and 3.61 g (11.1 mmol) of caesium carbonate suspended in 50 ml of tetrahydrofuran are placed in a 100 ml three-necked round-bottomed flask and the mixture is refluxed for 72 h. It is allowed to cool and is filtered, the filtrate is evaporated under reduced pressure and the residue is purified by chromatography on a column of silica gel, eluting with a 95/5/0.5 mixture of chloroform, methanol and aqueous ammonia. 0.83 g of an orange-coloured oil is obtained, which is suspended in 15 ml of ethanol, and 1.45 ml of a 37% solution of hydrobromic acid in acetic acid are added. 1.02 g of dihydrobromide are finally isolated.

Melting point: 295–305° C.

EXAMPLE 2

Compound 6

4-(6-Chloro-3-pyridazinyl)-1,4-diazabicyclo[3.2.2]_ nonane Hydrobromide (2:1)

0.88 g (7.0 mmol) of 1,4-diazabicyclo_[3.2.2]nonane and 0.52 g (3.5 mmol) of 3,6-dichloropyridazine in 25 ml of toluene are introduced into a 50 ml three-necked round-bottomed flask and the solution is refluxed for 24 h.

The solvent is evaporated off under reduced pressure and the residue is taken up in a 90/10 mixture of dichloromethane and methanol containing a few drops of aqueous ammonia, and the solution is eluted on silica gel with the same mixture of solvents.

0.58 g of compound in base form is obtained, which is converted into the dihydrobromide by addition of a 37% solution of hydrobromic acid in acetic acid.

After recrystallization from a 50/50 mixture of 2-propanol and methanol, 0.7 g of dihydrobromide is finally isolated.

Melting point: 291–293° C.

EXAMPLE 3

Compound 8

4-(6-Phenyl-3-pyridyl)-1,4-diazabicyclo[3.2.2] nonane Hydrobromide (2:1)

3.1. 3-Bromo-6-phenylpyridine 10 g (42.2 mmol) of 2,5-dibromopyridine, 5.2 g (42.2 mmol) of phenylboronic acid and 30 ml of benzene are introduced into a 250 ml three-necked round-bottomed flask, 1.5 g (1.3 mmol) of tetrakis(triphenylphosphine)palladium, 30 ml of benzene and 30 ml of aqueous 2M sodium carbonate solution and 1.4 ml of ethanol are added and the mixture is refluxed for 17 h.

The reaction medium is cooled and filtered, the organic phase is separated out after settling has taken place, the solvent is evaporated off under reduced pressure and the residue is purified by chromatography on silica gel, eluting with a 70/30 mixture of heptane and dichloromethane.

8.6 g of crude product are obtained, which product is recrystallized from 7 ml of ethanol. 5.6 g of pure product are thus obtained in the form of a white solid.

Melting point: 69–72° C.

3.2 4-(6-Phenyl-3-pyridyl)-1,4-diazabicyclo[3.2.2]_nonane Hydrobromide (2:1)

0.631 g (5 mmol) of 1,4-diazabicyclo[3.2.2]_nonane, 1.4 g (6 mmol) of 3-bromo-6-phenylpyridine, 2.28 g (7 mmol) of caesium carbonate, 45 mg (0.2 mmol) of palladium(II) acetate and 125 mg (0.2 mmol) of 2,2'-bis(diphenylphosphino)-1,1'-binaphthyl suspended in 40 ml of tetrahydrofuran are placed, under a nitrogen atmosphere, in a three-necked round-bottomed flask and the mixture is refluxed for 48 h.

The reaction medium is cooled and filtered and the solvent is evaporated off under reduced pressure. The residue obtained is purified by chromatography on silica gel, eluting with a 96/4/0.4 mixture of chloroform, methanol and aqueous ammonia. 0.47 g of crude product is obtained, which product is taken up in ether. An insoluble material is removed by filtration and the filtrate is concentrated under reduced pressure to give 0.42 g of product.

This product is suspended in 10 ml of ethanol and the solution obtained is treated with 0.6 ml of a 5M solution of hydrobromic acid in acetic acid. After 1 h, the precipitate is collected and rinsed with ethanol and then with ether. 0.519 g of product is thus obtained in the form of a white solid.

Melting point: 290–297° C.

EXAMPLE 4

Compound 9

4-(5-Bromo-3-pyridyl)-1,4-diazabicyclo[3.2.2] nonane Hydrobromide (2:1)

A solution containing 1.0 g (7.92 mmol) of 1,4-diazabicyclo[3.2.2]nonane and 2.82 g (11.89 mmol) of 3,5-dibromopyridine in 20 ml of tetrahydrofuran is added to a suspension of 71 mg (0.32 mmol) of palladium(II) acetate, 3.6 g (11.09 mmol) of caesium carbonate and 0.197 mg (0.32 mmol) of 2,2'-bis(diphenylphosphino)-1,1'-binaphthyl in 45 ml of tetrahydrofuran, in a 250 ml three-necked round-bottomed flask. The reaction medium is heated for 22 h.

The suspension is cooled and diluted with 65 ml of chloroform. The precipitate is removed by filtration and the filtrate is concentrated under reduced pressure to give 4.4 g of a dark brown solid. The product is purified by chromatography on silica gel, eluting with a 95/5/0.5 mixture of chloroform, methanol and aqueous ammonia. 1.25 g of pure product are obtained, which product is dissolved in 10 ml of ethanol and treated with 1.6 ml of a 5.7 M solution of hydrobromic acid in acetic acid at 0° C. 1.79 g of product are obtained, which product is recrystallized from 20 ml of an 86/14 mixture of ethanol/water. 1.14 g of product are thus obtained in the form of a pale yellow solid.

Melting point: 266–276° C.

EXAMPLE 5

Compound 10

4-(5-Phenyl-3-pyridyl)-1,4-diazabicyclo[3.2.2] nonane 0.87 g (3.1 mmol) of 4-(5-bromo-3-pyridyl)-1,4-diazabicyclo[3.2.2]nonane is introduced into a 50 ml three-necked round-bottomed flask, 0.39 g (3.15 mmol) of phenylboronic acid, 0.11 g (0.095 mmol) of tetrakis(triphenylphosphine)palladium, 3.3 ml of aqueous 2 M sodium carbonate solution, 6.5 ml of benzene and 0.15 ml of ethanol are added and the mixture is refluxed for 16 h.

The reaction medium is cooled, diluted with 90 ml of benzene and filtered. The organic phase is separated out and the solvent is evaporated off under reduced pressure. The residue is purified by chromatography on a column of silica gel, eluting with a 95/5/0.5 mixture of chloroform, methanol and aqueous ammonia. 0.80 g of an orange-coloured oil is obtained, which is crystallized from 4 ml of petroleum ether. 0.617 g of product is thus obtained in the form of an off-white solid.

Melting point: 85–88° C.

EXAMPLE 6

Compound 7

4-(6-Chloro-2-pyrazinyl)-1,4-diazabicyclo[3.2.2] nonane 0.30 g (2.0 mmol) of 1,4-diazabicyclo[3.2.2]_nonane, 0.30 g (2.0 mmol) of 2,6-dichloropyrazine, 3 ml of aqueous 50% sodium hydroxide solution and 64.4 mg (0.2 mmol) of tetrabutylammonium bromide in 3 ml of toluene are introduced into a 25 ml three-necked round-bottomed flask and the reaction medium is heated at 60° C. for 4 h.

0.30 g (2.0 mmol) of 2,6-dichloropyrazine and 64.4 mg (0.2 mmol) of tetrabutylammonium bromide are added and heating is continued for 18 h.

The organic phase is separated out, water is added and the mixture is extracted with chloroform. The solvent is evaporated off under reduced pressure and the residue obtained is purified by chromatography on a column of silica gel, eluting with a 95/5/0.5 mixture of chloroform, methanol and aqueous ammonia, and the product obtained is crystallized from 1.5 ml of diisopropyl ether.

0.17 g of product is obtained.

Melting point: 80° C.

EXAMPLE 7

Compound 12

4-(6-Phenyl-3-pyridazinyl)-1,4-diazabicyclo[3.2.2] nonane Hydrobromide (2:1)

0.477 g (2.0 mmol) of 4-(6-chloro-3-pyridazinyl)-1,4-diazabicyclo[3.2.2]nonane, 0.293 g (2.4 mmol) of phenylboronic acid, 69 mg (0.06 mmol) of tetrakis (triphenylphosphine)palladium, 2 ml of an aqueous 2M sodium carbonate solution and 0.1 ml of ethanol are introduced into a 25 ml three-necked round-bottomed flask and the reaction medium is refluxed for 17 h.

The organic phase is separated out after settling has taken place, washed with water and evaporated under reduced pressure, and the residue is purified by chromatography on silica gel, eluting with a 95/5/0.5 mixture of chloroform, methanol and aqueous ammonia.

0.49 g of product is obtained in the form of an oil, which is taken up in 5 ml of ethanol and treated with 0.7 ml of a 5M solution of hydrobromic acid in acetic acid. The precipitate is filtered off and rinsed with ethanol and then with ether.

0.551 g of white solid is thus obtained.

Melting point: 295–298° C.

The table which follows illustrates the chemical structures and the physical properties of a number of compounds of the invention.

In the "$R_1$" column, "3,4—$OCH_2O$—$C_6H_3$" denotes a 3,4-methylenedioxyphenyl, or 1,3-benzodioxol-5-yl group and "4—$C_6H_5$—$C_6H_4$" denotes a 4-biphenylyl group.

In the "salt" column, "—" denotes a compound in base form, "HBr" denotes a hydrobromide and "HCl" denotes a hydrochloride; the acid:base molar ratio is indicated adjacent thereto.

In the "m.p. (° C.)" column, "(d)" denotes a melting point with decomposition.

TABLE (I)

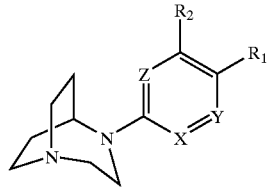

| No. | X | Y | Z | $R_1$ | $R_2$ | Salt | m.p. (° C.) |
|---|---|---|---|---|---|---|---|
| 1 | CH | N | CH | H | H | HBr 2:1 | 295–305 |
| 2 | CH | N | CH | Cl | H | HBr 2:1 | 264–265 |
| 3 | N | CH | CCl | H | H | HCl 2:1 | 300–303 |
| 4 | CH | N | N | H | H | HBr 2:1 | 293–297 |
| 5 | CCl | N | N | H | H | HBr 1:1 | 279–280 |
| 6 | N | N | CH | Cl | H | HBr 2:1 | 291–293 |
| 7 | CH | N | N | H | Cl | — | 80 |
| 8 | CH | N | CH | $C_6H_5$ | H | HBr 2:1 | 290–297 |
| 9 | CH | N | CH | H | Br | HBr 2:1 | 266–276 |
| 10 | CH | N | CH | H | $C_6H_5$ | — | 85–88 |
| 11 | CH | N | CH | $CH_3O$ | H | HBr 2:1 | 170–172 |
| 12 | N | N | CH | $C_6H_5$ | H | HBr 2:1 | 295–298 |
| 13 | N | N | CH | 3,4-$OCH_2O$—$C_6H_3$ | H | HBr 2:1 | 296 (d) |
| 14 | N | N | CH | 4-$CH_3$—$C_6H_4$ | H | HBr 2:1 | 241–245 |
| 15 | N | N | CH | 3,5-$(CF_3)_2$—$C_6H_3$ | H | HBr 2:1 | 243 (d) |
| 16 | N | N | CH | 4-$C_6H_5$—$C_6H_4$ | H | HBr 2:1 | 310 (d) |
| 17 | N | N | CH | 4-F—$C_6H_4$ | H | HBr 2:1 | 234 |
| 18 | N | N | CH | 4-$CF_3O$—$C_6H_4$ | H | HBr 2:1 | 110 (d) |
| 19 | N | N | CH | 3-$CF_3$—$C_6H_4$ | H | HBr 2:1 | 200–202 |
| 20 | N | N | CH | 3-Cl—$C_6H_4$ | H | HBr 2:1 | 285 (d) |
| 21 | N | N | CH | 3-$NO_2$—$C_6H_4$ | H | HBr 2:1 | 305–313 (d) |
| 22 | N | N | CH | H | H | HBr 2:1 | 317 (d) |
| 23 | N | N | CH | 3-$CH_3CO$—$C_6H_4$ | H | HBr 2:1 | 281 (d) |
| 24 | CH | N | CH | 4-F—$C_6H_4$ | H | HBr 2:1 | 284–292 |
| 25 | CH | N | CH | 4-$OCH_3$—$C_6H_4$ | H | HBr 2:1 | 246–251 |
| 26 | CH | N | CH | H | 3-$CF_3$—$C_6H_4$ | HBr 2:1 | 315 |
| 27 | CH | N | CH | H | 3,4-$OCH_2O$— $C_6H_3$ | HBr 2:1 | 280 |
| 28 | CH | N | CH | H |  | HBr 2:1 | 325 |
| 29 | CH | N | CH | H | 4-F—$C_6H_4$ | HBr 2:1 | 326 |
| 30 | CH | N | CH | H | 3-$CH_3CO$—$C_6H_4$ 3-Cl—$C_6H_4$ | HBr 2:1 | 298 |
| 31 | CH | N | CH | H | 3-$CH_3O$—$C_6H_4$ | HBr 2:1 | 288 |
| 32 | CH | N | CH | H | 2-$CH_3$—$C_6H_4$ | HBr 2:1 | 293 |
| 33 | CH | N | CH | H | 4-$CH_3$—$C_6H_4$ | HBr 2:1 | 320 |
| 34 | CH | N | CH | H | 2-Cl—$C_6H_4$ | HBr 2:1 | 277–278 |
| 35 | CH | N | CH | H | 4-$CH_3O$—$C_6H_4$ | HBr 2:1 | 294 |
| 36 | CH | N | CH | H | 2-$CH_3O$—$C_6H_4$ | HBr 2:1 | 320 |
| 37 | CH | N | CH | H | 4-$CF_3O$—$C_6H_4$ | HBr 2:1 | 325 |
| 38 | CH | N | CH | H | 4-$CH_3S$—$C_6H_4$ | HBr 2:1 | 315 |

TABLE-continued (I)

| No. | X | Y | Z | $R_1$ | $R_2$ | Salt | m.p. (° C.) |
|---|---|---|---|---|---|---|---|
| 39 | CH | N | CH | 3,4-OCH$_2$O—C$_6$H$_3$ | H | | |
| 40 | CH | N | CH | 4-CH$_3$—C$_6$H$_4$ | H | | |
| 41 | CH | N | CH | 3-CH$_3$—C$_6$H$_4$ | H | | |
| 42 | CH | N | CH | 3-F—C$_6$H$_4$ | H | | |
| 43 | CH | N | CH | 3,4-(OCH$_3$)$_2$—C$_6$H$_3$ | H | | |
| 44 | CH | N | CH | 2-CH$_3$O—C$_6$H$_4$ | H | | |
| 45 | CH | N | CH | 2-F—C$_6$H$_4$ | H | | |
| 46 | CH | N | CH | 4-CF$_3$—C$_6$H$_4$ | H | | |
| 47 | CH | N | CH | 3-CH$_3$O—C$_6$H$_4$ | H | | |

The compounds of the invention underwent tests which demonstrated their therapeutic properties.

Thus, they were studied as regards their affinity with respect to nicotinic receptors containing the $\alpha_4\beta_2$ subunit according to the methods described by Anderson and Arneric, *Eur. J. Pharmacol* (1994) 253 261, and by Hall et al., *Brain Res.* (1993) 600 127.

Male Sprague Dawley rats weighing 150 to 200 g are decapitated and the entire brain is removed quickly, homogenized in 15 volumes of 0.32 M sucrose solution at 4° C. and then centrifuged at 1000×g for 10 min. The pellet is discarded and the supernatant is centrifuged at 20,000×g for 20 min at 4° C. The pellet is recovered and homogenized using a Polytron™ mill in 15 volumes of double-distilled water at 40° C., followed by centrifugation at 8000×g for 20 min. The pellet is discarded and the supernatant and the "buffy coat" are centrifuged at 40,000×g for 20 min, the pellet is recovered, resuspended in 15 ml of double-distilled water at 4° C. and centrifuged again at 40,000×g, before being stored at −80° C.

On the day of the experiment, the tissue is thawed slowly and suspended in 3 volumes of buffer. 150 μl of this membrane suspension are incubated at 4° C. for 120 min in the presence of 100 μl of 1 nM [$^3$H]cytisine in a final volume of 500 μl of buffer, in the presence or absence of test compound. The reaction is stopped by filtration on Whatman GF/B™ filters pretreated with polyethyleneimine, the filters are rinsed with 2×5 ml of buffer at 4° C. and the radioactivity retained on the filter is measured by liquid scintigraphy. The non-specific binding is determined in the presence of 10 μM (−)-nicotine; the non-specific binding represents 75 to 85% of the total binding recovered on the filter. For each concentration of test compound, the percentage of inhibition of the specific binding of [$^3$H]cytisine is determined, followed by calculating the IC$_{50}$ value, which is the concentration of compound which inhibits the specific binding by 50%.

The IC$_{50}$ values for the purest compounds of the invention is between 0.001 and 0.013 μM.

The compounds of the invention were also studied as regards their affinity with respect to nicotinic receptors containing the α7 subunit, according to the methods described by Marks and Collins, *J. Pharmacol. Exp. Ther.* (1982) 22 564 and Marks et al., *Mol. Pharmacol.* (1986) 30 427.

Male OFA rats weighing 150 to 200 g are decapitated, the entire brain is removed quickly and homogenized using a Polytron™ mill in 15 volumes of a 0.32 M sucrose solution at 4° C., followed by centrifugation at 1000×g for 10 min. The pellet is discarded and the supernatant is centrifuged at 8000×g for 20 min at 4° C. The pellet is recovered and homogenized using a Polytron™ mill in 15 volumes of double-distilled water at 40° C., followed by centrifugation at 8000×g for 20 min. The pellet is discarded and the supernatant and the buffy coat are centrifuged at 40,000×g for 20 min. The pellet is recovered, resuspended with 15 volumes of double-distilled water at 40° C. and centrifuged again at 40,000×g for 20 min, before storing it at −80° C.

On the day of the experiment, the tissue is thawed slowly and suspended in 5 volumes of buffer. 150 μl of this membrane suspension is preincubated at 370° C. for 30 min, in the dark, in the presence or absence of the test compound. Next, the membranes are incubated for 60 min at 370° C., in the dark, in the presence of 50 μl of 1 nM [$^3$H]α-bungarotoxin in a final volume of 250 μl of 20 mM HEPES, 0.05% polyethyleneimine buffer. The reaction is stopped by filtration through Whatman GF/C™ filters pretreated for 3 hours with 0.5% polyethyleneimine. The filters are rinsed with 2×5 ml of buffer at 40° C. and the radioactivity retained on each filter is measured by liquid scintigraphy. The non-specific binding in the presence of α-bungarotoxin at 1 μM final is determined; the non-specific binding represents about 60% of the total binding recovered on the filter. For each concentration of test compound, the percentage of inhibition of the specific binding of [$^3$H] α-bungarotoxin is determined, followed by calculation of the IC$_{50}$ value, which is the concentration of compound which inhibits the specific binding by 50%.

The IC$_{50}$ values for the purest compounds of the invention are between 0.002 and 0.75 μM.

The compounds of the invention were also studied as regards their affinity with respect to peripheral nicotinic receptors of ganglion type, according to the method described by Houghtling et al., *Mol. Pharmacol.* (1995) 48 280–287. The capacity of a compound to displace [$^3$H]-epibatidine from bovine adrenal gland membranes measures its affinity for this receptor.

Bovine adrenal glands stored at −80° C. are thawed and homogenized using a Polytron™ mill, in 20 volumes of 50 mM Tris-HCl buffer at pH 7.4 at 4° C., followed by centrifugation at 35,000×g for 10 min. The supernatant is discarded and the pellet is resuspended in 30 volumes of 50 mM Tris-HCl buffer at 4° C. and re-homogenized, after which it is recentrifuged at 35,000×g for 10 min. The final pellet is taken up in 10 volumes of Tris-HCl buffer at 4° C. 100 µl of membrane, i.e. 10 mg of fresh tissue, are incubated at 24° C. for 3 h in the presence of 50 µl of 0.66 nM final [$^3$H]-epibatidine in a final volume of 250 µl of buffer, in the presence or absence of test compound. The reaction is stopped by diluting the samples with 50 µM Tris-HCl buffer at pH 7.4 at 4° C., followed by filtration on Whatman GF/C™ filters pretreated for 3 hours with 0.5% polyethyleneimine. The filters are rinsed twice with 5 ml of buffer and the radioactivity retained on the filter is measured by liquid scintigraphy. The non-specific binding is determined in the presence of 2 mM final (−)-nicotine; the non-specific binding represents 30 to 40% of the total binding recovered on the filter. For each concentration of test compound, the percentage of inhibition of the specific binding of [$^3$H]-epibatidine is determined, followed by calculating the $IC_{50}$ value, which is the concentration of compound which inhibits the specific binding by 50%.

The $IC_{50}$ values for the compounds of the invention are between 0.06 and 20 µM.

The results of the preceding tests show that certain compounds of the invention are selective ligands for the $\alpha_4 B_2$, $\alpha_7$ or $\alpha_3$ subunits of the nicotinic receptor and that others are mixed $\alpha_4 B_2$ and $\alpha_7$, $\alpha_4 B_2$ and $\alpha_3$, or $\alpha 7$ and $\alpha_3$.

Finally, the compounds of the invention underwent studies which demonstrated their analgesic properties. Thus, they were studied in the hotplate model, according to the method by Eddy and Leimbach, *J. Pharmacol. Exp. Ther.* (1953) 107 385–393 with the aim of investigating and quantifying any analgesic effect. Mice weighing 20 to 30 g are subjected to a heat stimulus by contact of the paws with a plate kept at a constant temperature of 57.5° C. by a thermostatically controlled water bath. The reaction time to the pain, which is manifested by licking of the paws or jumping, is measured. Thus, after the interval of pretreatment carried out subcutaneously or orally (each batch consisting of eight animals for the same pretreatment), the mice are placed individually on the plate and the reaction time to the pain is measured. The animal is removed from the plate immediately after manifestation of the pain. The maximum exposure time to the stimulus is 30 seconds.

The mean reaction time and the standard error of mean (s.e.m.) are expressed for each batch. A non-parametric variance analysis (Kruskal-Wallis) is carried out on the entire batch. A Wilcoxon test allows comparison of each treated batch with the control batch. The differences are considered as statistically significant at the 5% threshold.

This reaction time is significantly increased by the analgesics mainly with central effects.

The compounds of the invention show activity in this test at doses of between 0.3 and 30 mg/kg intraperitoneally or orally.

The results of the various tests suggest the use of the compounds in the treatment or prevention of disorders associated with a dysfunction of the nicotinic receptors, in particular on the central nervous system or the gastrointestinal system.

On the central nervous system, these disorders comprise cognitive impairment, more specifically memory impairment, but also attention impairment, associated with Alzheimer's disease, pathological ageing (Age Associated Memory Impairment, AAMI), Parkinson's disease, trisomy 21 (Down's syndrome), Korsakoff's alcoholic syndrome, vascular dementia (multi-infarct dementia, MID) and attention deficit/hyperactivity disorder, ADHD).

The compounds of the invention may also be useful in the treatment of the motor disorders observed in Parkinson's disease or other neurological diseases such as Huntington's chorea, Tourette's syndrome, tardive dyskinesia and hyperkinesia.

The compounds of the invention can also constitute a curative or symptomatic treatment for cranial or medullary accidents and traumas, cerebrovascular accidents and cerebral hypoxic episodes, as well as other acute or chronic neurodegenerative diseases.

They can be used in psychiatric pathologies: schizophrenia, depression, anxiety, panic attacks, compulsive and obsessive behaviour.

They can prevent the symptoms due to withdrawal from tobacco, from alcohol and from various substances which induce a dependence, such as cocaine, LSD, cannabis and benzodiazepines.

Finally, they can be useful for the treatment of acute and neuropathic pain.

On the gastrointestinal system, the compounds of the invention may be useful in the treatment of Crohn=s disease, ulcerous colitis, irritable bowel syndrome and obesity.

To this end, the compounds of the invention can be in any composition form which is suitable for enteral, parenteral or transdermal administration, such as tablets, sugar-coated tablets, gel capsules, wafer capsules, drinkable or injectable suspensions or solutions such as syrups or ampules, transdermal patches, etc., combined with suitable excipients, and dosed to allow a daily administration of from 0.01 to 20 mg/kg.

What is claimed is:

1. A compound of general formula (I)

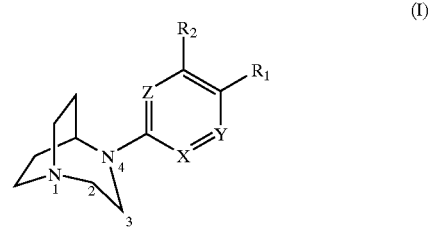

in which
one of the symbols X, Y and Z represents a nitrogen atom, another represents a group of formula C—R$_3$ and the third represents a nitrogen atom or a group of formula C—R$_4$, R$_3$ and R$_4$ represent, independently of each other, a hydrogen or halogen atom or a trifluoromethyl, cyano, hydroxyl, (C$_1$–C$_6$)alkyl or (C$_1$–C$_6$)alkoxy group, R$_1$ and R$_2$ represent, independently of each other, a hydrogen or halogen atom or a trifluoromethyl, cyano, hydroxyl, (C$_1$–C$_6$)alkyl or (C$_1$–C$_6$)alkoxy group or a phenyl group optionally substituted with a halogen atom, with a trifluoromethyl group, with a cyano group, with a nitro group, with a hydroxyl group, with a (C$_1$–C$_6$)alkyl group, with a (C$_1$–C$_6$)alkoxy group, with an acetyl group, with a methylenedioxy group, with a trifluoromethoxy group, with a methylthio group or with a phenyl group, in the form of a base or of an addition salt with an acid.

2. A compound according to claim 1 wherein the heterocycle containing X, Y and Z is a 3-pyridyl group.

3. A compound according to claim 1 wherein the heterocycle containing X, Y and Z is a 3-pyridazinyl group.

4. A method for the treatment of disorders associated with a dysfunction of the nicotinic receptors which comprises administering to a patient in need of such treatment an effective amount of a compound according to any one of claims 1 to 3.

5. A pharmaceutical composition which comprises a compound according to any one of claims 1 to 3 together with an excipient.

* * * * *